United States Patent [19]

Hosaka et al.

[11] 4,059,637
[45] Nov. 22, 1977

[54] METHOD FOR EXTRACTION OF DIHYDROPEROXIDE

[75] Inventors: Hirokazu Hosaka; Kenji Tanimoto, both of Hirakata; Hiromichi Okabe; Kunthiko Tanaka, both of Ibaraki; Yuji Ueda, Izumiotsu; Iwao Dohgane, Ashiya, all of Japan

[73] Assignee: Sumitomo Chemical Company, Limited, Osaka, Japan

[21] Appl. No.: 607,020

[22] Filed: Aug. 22, 1975

[30] Foreign Application Priority Data

Sept. 3, 1974 Japan .................. 49-101634

[51] Int. Cl.² .......................... C07C 179/02
[52] U.S. Cl. .................. 260/610 A
[58] Field of Search ............ 260/610 A, 610 B

[56] References Cited

U.S. PATENT DOCUMENTS

| 2,856,432 | 10/1958 | Conner et al. | 260/610 A |
| 2,856,433 | 10/1958 | Thompson | 260/610 A |
| 3,190,923 | 6/1965 | Sodomann et al. | 260/610 A |
| 3,190,924 | 6/1965 | Sodomann et al. | 260/610 B |

FOREIGN PATENT DOCUMENTS

| 727,498 | 4/1955 | United Kingdom | 260/610 B |
| 743,736 | 1/1956 | United Kingdom | 260/610 A |

Primary Examiner—James O. Thomas, Jr.
Assistant Examiner—W. B. Lone
Attorney, Agent, or Firm—Stevens, Davis, Miller & Mosher

[57] ABSTRACT

A method for extracting a dihydroperoxide of a dialkylbenzene of the formula,

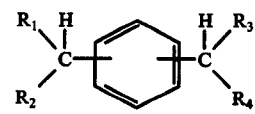

wherein each $R_1$, $R_2$, $R_3$ and $R_4$ is independently a lower alkyl group, from an aqueous alkali solution of the said dihydroperoxide with at least one organic solvent selected from the group consisting of $C_4$–$C_{10}$ ketones, $C_4$–$C_{10}$ ethers and $C_4$–$C_8$ alcohols, which comprises extracting the dihydroperoxide by a countercurrent multi-stage extraction at a temperature between 0° and 85° C with a temperature gradient, the aqueous alkali solution being fed to the lower temperature zone, the organic solvent being fed to the higher temperature zone, and each aqueous alkali solution and organic solvent being fed countercurrently, whereby the dihydroperoxide is obtained in the form of organic solvent solution from the lower temperature zone.

6 Claims, 1 Drawing Figure

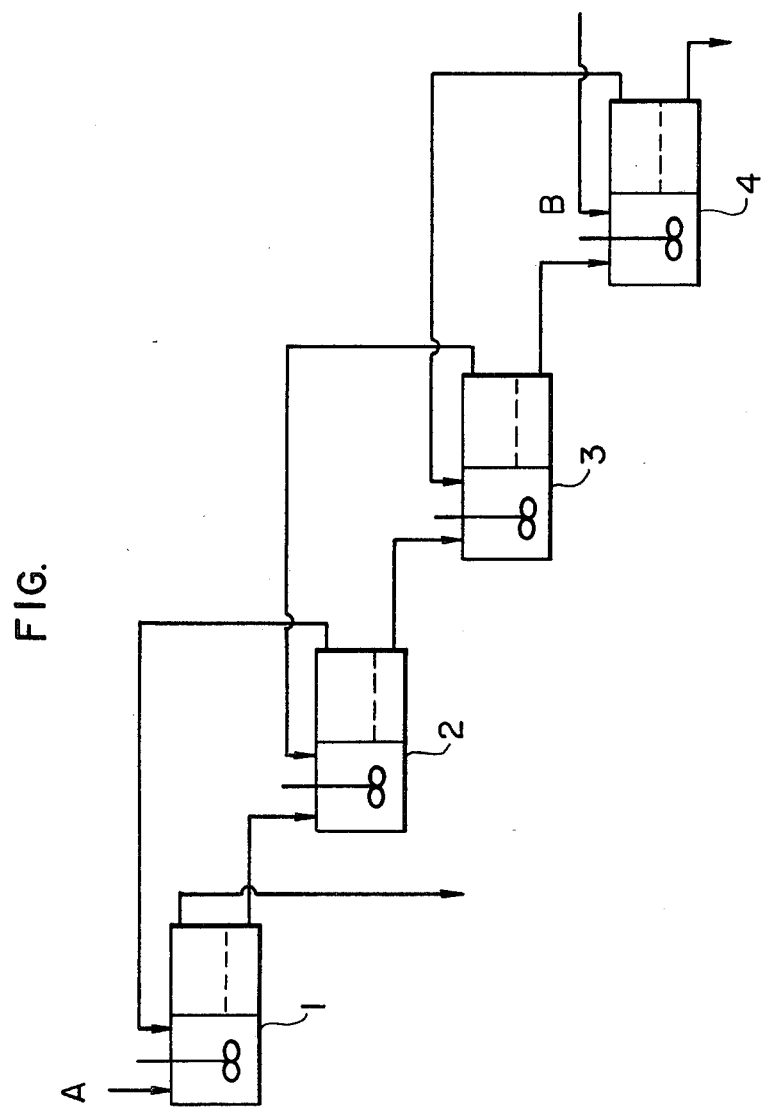

METHOD FOR EXTRACTION OF DIHYDROPEROXIDE

The present invention relates to a method for extracting and recovering dialkylbenzene dihydroperoxide from aqueous alkali solutions thereof with a high efficiency. More particularly, the invention relates to an industrially advantageous method for extracting and recovering the dihydroperoxide in a high yield and high purity by carrying out countercurrent multistage extraction with a temperature gradient from 0° to 85° C.

A method which comprises oxidizing dialkylbenzenes into dihydroperoxide thereof and cleaving the dihydroperoxide into resorcinol and/or hydroquinone is attracting attention as a novel and advantageous preparation of resorcinol and/or hydroquinone.

The alkylbenzenes which are used for this purpose include for example diisopropylbenzene, di-sec-butylbenzene, isopropyl-sec-butylbenzene and the like, of which diisopropylbenzene is most popular. The present invention will be illustrated with reference to the diisopropylbenzene.

In the preparation of resorcinol and hydroquinone from diisopropylbenzene as a starting material, the diisopropylbenzene is first oxidized with oxygen or air. The resulting oxidation solution is a mixture of the objective diisopropylbenzene dihydroperoxide (referred to as DHPO hereinafter), other hydroperoxides (HPO), by-products and unreacted material (diisopropylbenzene). The hydroperoxides other than DHPO include diisopropylbenzene monohydroperoxide (referred to as MHPO hereinafter), 2-hydroxy-2-propylcumene hydroperoxide (referred to as CHPO hereinafter), acethylcumene hydroperoxide (referred to as AHPO hereinafter) and the like. It is therefore necessary to separate DHPO from the oxidation solution and there are many methods for separating DHPO from the oxidation solution. Of those, a very effective method having an excellent selectivity is one disclosed in British Pat. No. 727,498 which comprises treating the oxidation solution with aqueous alkali solutions such as 1 to 15% aqueous solution of sodium hydroxide. According to this method, DHPO and a part of CHPO are extracted into the aqueous sodium hydroxide solution and others remain in the oily layer. However, the DHPO in the aqueous sodium hydroxide layer can not be converted to resorcinol and/or hydroquinone as it is, and it is necessary to dissolve the DHPO in organic solvents by some methods prior to the cleavage reaction.

There are two methods for this purpose, one being a method which comprises neutralizing said aqueous sodium hydroxide solution with acids and extracting the free DHPO with organic solvents, and the other being a method which comprises extracting DHPO directly from said aqueous sodium hydroxide solution with special organic solvent such as methyl isobutyl ketone (MIBK) and the like. In the former neutralization method, sodium hydroxide consumed in an extremely large amount becomes useless by the neutralization, and a large amount of acid is also required for the neutralization. Therefore the method becomes expensive and is not advantageous industrially. Contrary to this, the latter method needs no acids for neutralization and a large portion of the residual aqueous sodium hydroxide layer after extraction can be recycled to the extraction step of oxidation solution. Consequently, the latter method for recovering DHPO is very advantageous in terms of economy. The direct extraction method, however, includes a very serious problem when applied according to the well-known technique. That is, DHPO is recovered from its aqueous alkali solution by contacting the solution with organic solvents at a temperature as high as 75° to 85° thereby transferring the DHPO from the aqueous solution into the organic layer. But, the DHPO cannot transfer into the organic layer without an extremely lowered retention rate. The retention rate of DHPO is calculated according to the following equation.

$$\text{Retention rate} = \frac{\text{total amount of DHPO in the aqueous alkali layer and the organic layer after extraction}}{\text{amount of DHPO in the aqueous alkali solution before extraction}} \times 100$$

The reduction in retention rate becomes particularly remarkable as number of recycles of the aqueous alkali solution increases. This seems possibly due to that the DHPO decomposes in the aqueous alkali solution into mainly CHPO, di(2-hydroxy-2-propyl)-benzene (referred to as DCA hereinafter), organic acids and the like.

The deterioration of DHPO on the extraction step not only causes a loss in DHPO but also gives an adverse effect on the cleavage reaction of the DHPO-containing organic extract. That is, in the cleavage reaction for production of resorcinol and hydroquinone, contamination of the organic extract with the impurities having a 2-hydroxy-2-propyl group, for example CHPO and DCA, disturbs the cleavage reaction of DHPO and reduces the yield to a large extent.

Thus, how to recover DHPO advantageously from its aqueous alkali solution without any decomposition of the DHPO becomes very important for the preparation of resorcinol and/or hydroquinone via the DHPO.

As a result of detailed investigation on the deterioration of DHPO under alkaline conditions, it has been found that the deterioration of DHPO gradually increases as the extracting temperature increases, and that the deterioration becomes very remarkable when the temperature passes over 70° C.

Therefore, the deterioration can practically be avoided when the organic solvent extraction is carried out at low temperatures, but an extremely large amount of organic solvent is required, because the distribution coefficient of DHPO in organic solvent is very small at low temperatures. This is due to the fact that DHPO is dissolved in the aqueous alkali solution not as such but in the form of salt and therefore that the transfer of DHPO into organic solvents is possibly an extraction accompanied by reaction thus requiring a relatively high temperature. In the low temperature extraction, a large amount of solvent which requires large scale equipments in the subsequent steps must be used, and moreover the solvent must be recovered for reuse with an extemely large quantity of steam, electric power and the like. Therefore, this process can not be applied advantageously to an industrial scale.

The inventors have found a method for recovering DHPO with organic solvents which neither causes the defects nor deterioration as mentioned above.

The present invention provides a method for extracting a dihydroperoxide of a dialkylbenzene of the formula (I),

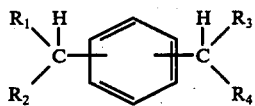

wherein each $R_1$, $R_2$, $R_3$ and $R_4$ is independently a lower alkyl group, from an aqueous alkali solution of the said dihydroperoxide with at least one organic solvent selected from the group consisting of $C_4$–$C_{10}$ ketones, $C_4$–$C_{10}$ ethers and $C_4$–$C_8$ alcohols, which comprises extracting the dihydroperoxide by a countercurrent multi-stage extraction at a temperature between 0° and 85° C with a temperature gradient, the aqueous alkali solution being fed to the lower temperature zone, the organic solvent being fed to the higher temperature zone, and each aqueous alkali solution and organic solvent being fed countercurrently, whereby the dihydroperoxide is obtained in the form of organic solvent solution from the lower temperature zone.

More concretely, the invention provides a method for extracting a dihydroperoxide of a dialkylbenzene of the above formula (I), from an aqueous alkali solution of the said dihydroperoxide, which comprises feeding the aqueous alkali solution to one side of an extraction zone together with countercurrent feed of at least one organic solvent selected from the group consisting of $C_4$–$C_{10}$ ketones, $C_4$–$C_{10}$ ethers and $C_4$–$C_8$ alcohols to the other side of extraction zone, the extraction zone having a multi-stage of a temperature between 0° and 85° C with a temperature gradient, the aqueous alkali solution being fed to a lower temperature zone and the organic solvent being fed to a higher temperature zone, whereby the dihydroperoxide is obtained in the form of the organic solvent solution from the lower temperature zone.

The present invention will be illustrated in more details as follows.

The aqueous alkali solution to be extracted according to the method of the present invention is a solution obtained by oxidation of the dialkylbenzene of the formula (I) with oxygen or oxygen-containing gas according to a conventional method, for example, disclosed in British Pat. No. 727,498, and then by extraction of the oxidation solution with an alkali solution according to a conventional method, for example, also disclosed in the above-said British Patent. The resulting aqueous alkali solution can be treated to remove oxidation by-products having 2-hydroxy-2-propyl group prior to the extraction according to the present invention. For example, the solution containing DHPO and a small amount of the 2-hydroxy-2-propyl group having compounds such as CHPO and DCA is treated at below 30° C with an organic solvent such as isopropyl ether and methyl isobutyl ketone to transfer CHPO and DCA into the organic solvent layer, the most part of DHPO remaining in the aqueous alkali solution (disclosed in, for example, German Offenlegungsschrift No. 2,331,892). The concentration of the dihydroperoxide in the aqueous alkali solution is about 3 to 20% by weight. The extraction of the present invention fundamentally comprises extracting the aqueous alkali solution having a high DHPO content at a plate kept at a lower temperature, carrying out the extraction at increasingly elevated temperatures as the DHPO content becomes low and extracting the solution having the lowest DHPO content at a plate kept at a higher temperature.

In this multi-stage extraction, temperature differences are set up between adjacent plates so that a temperature gradient may be formed between the two extreme ends, with 0° C at one end and with 85° C at the other end. It is desirable in terms of extraction efficiency and operation to control the lower temperature zone (inlet for the aqueous alkali solution) at 0° to 50° C, preferably about 25° to 45° C and to control the higher temperature zone (outlet for the residual aqueous alkali solution) at 50° to 85° C, preferably about 55° to 75° C. The temperature at each plate and temperature difference between adjacent plates may optionally be selected depending upon extracting conditions, for example the kind of aqueous alkali solution containing DHPO, and proportion of the aqueous alkali solution and solvents used.

It is desirable to set up the temperature at each plate so that a smooth slope of temperature may be formed between the low and high temperature zones. That is, it is desirable to set up the temperature so that the temperature of aqueous alkali layer gradually increases as the layer is countercurrent passes through the plates. For this purpose, it is desirable to avoid a large or uneven temperature difference between the adjacent plates. For example, in the extraction with a six-stage (theoretical plate) extractor where temperatures of the inlet plate for aqueous alkali solution and of the outlet plate for residual aqueous alkali solution are fixed at 40° and 60° C, respectively. The preferred temperature difference between the adjacent plates is about 3° to 5° C.

The temperature difference between adjacent plates can be set up by fixing a heating or cooling device to each plate, for example by circulating warm water or cold water through the jacket of extractors. Alternatively, the temperature difference can also be set up by feeding pre-heated organic solvents and pre-cooled aqueous alkali liquors containing DHPO to the extractor in a countercurrent process, and the pre-heating and pre-cooling process may be combined with the above mentioned external heating and cooling process.

In the present method, two to 12 plates (theorethical plate) are required for extraction. Only one plate gives no extraction effect and more than twelve plates do not give the effect enough to compensate for such number of plates. After all, the most desirable number of plates is three to eight in terms of extraction efficiency and expense. The shape of extractor is not particularly limited, and a tower-type countercurrent continuous extractor or a combination of mixer-settler type extractors may be used. In case of the tower-type extractor, the practical number of plates must be determined to meet the plate efficiency.

The organic solvents used in the present invention include a $C_4$–$C_{10}$ ketone, $C_4$–$C_8$ alcohol, and $C_4$–$C_{10}$ ether. Examples of the solvents include methyl ethyl ketone, methyl n-propyl ketone, methyl isopropyl ketone, methyl n-butyl ketone, methyl isobutyl ketone, di-n-propyl ketone, di-isobutyl ketone, ethyl n-butyl ketone, butanol, pentanol, ethyl ether, isopropyl ether, n-butyl ether and like. Of those, methyl ethyl ketone, methyl isopropyl ketone, methyl isobutyl ketone and isopropyl ether are particularly effective. These solvents may be used alone or in combination, however it is preferred to use them alone in terms of ease of recovery of the solvent.

Amount of solvents used may suitably be selected depending upon the kind of the solvents, DHPO content of aqueous alkali solution and treating temperatures. In general, however, amounts of one to five times by weight based on the DHPO-containing aqueous alkali solution are used.

The effect which is obtained in the extraction of DHPO from its aqueous alkali solution according to the present invention is very remarkable as mentioned hereinafter. For example, according to the conventional extraction technique wherein the DHPO is extracted from its aqueous alkali solution at a temperature as high as 75° 1 to 85° C, the retention rate of DHPO is as low as 84%. But the retention rate according to the invention is as high as about 97%, which means that the quality deterioration of DHPO is restricted to a negligible extent. Particularly, this difference between the retention rates becomes further large when the residual aqueous alkali solution is recycled to the alkali extraction step as an aqueous alkali solution for extracting the oxidation solution. The retention rate of DHPO falls down to about 55% according to the conventional technique but it keeps a very high level of about 94% according to the present invention.

As mentioned above, the present invention was illustrated with reference to diisopropylbenzene, but this invention is of course applicable similarly to other compounds represented by the formula (I).

FIG. 1 is one example of the embodiments of the present invention. The numbers 1 to 4 each represents a mixer-settler and the symbols A and B represent the aqueous caustic soda liquor inlet and the organic solvent inlet.

The present invention will be illustrated specifically with reference to the following examples. All percentages and parts in the examples are by weight.

EXAMPLE 1

Countercurrent multi-stage extraction was carried out using a combination of four mixer-settler type extractors (Nos. 1 to 4) as shown in FIG. 1. DHPO-containing aqueous alkali solution as a material was prepared by extracting the oxidation solution of m-diisopropylbenzene with an 8% aqueous caustic soda solution and then extracting the aqueous extract with methyl isobutyl ketone (MIBK) at 20° C to remove CHPO and the like in advance. The DHPO-content and CHPO-content of the solution as a material were 11.3 and 0.5%, respectively.

The aqueous caustic soda solution was charged in the mixer-settler No. 1 at the liquor inlet A at a feed rate of 100 parts/hr. The extracting solvent, MIBK, was charged in the mixer-settle No. 4 at the liquor inlet B at a feed rate of 200 parts/hr.

The aqueous alkali layer separated in the mixer-settler No. 1 passed into the mixer-settler No. 2. In the same manner, the aqueous alkali layers separated in the mixer-settlers No. 2 and No. 3 passed into the adjacent mixer-settlers No. 3 and No. 4, respectively.

The aqueous alkali layer separated in the mixer-settler No. 4 (residual aqueous alkali liquor) can be recycled as an aqueous alkali solution for extracting the oxidation solution of m-diisopropylbenzene.

The MIBK layer separated in the mixer-settler No. 4 passed into the mixer-settler No. 3. In the same manner, the MIBK layers separated in the mixer-settlers No. 3 and No. 2 passed into the adjacent mixer-settlers No. 2 and No. 1, respectively. The MIBK layer separated in the mixer-settler No. 1 was an organic solution containing DHPO and supplied to the subsequent cleavage step as a material for preparation of resorcinol. The temperatures of mixer-settlers were controlled at 42°, 48°, 55° and 62° C for No. 1, No. 2, No. 3 and No. 4, respectively.

After the continuous extracting operation, the residual aqueous alkali liquor was obtained from the mixer-settler No. 4 in a proportion of 89 parts on the average per hour and its DHPO content was 0.89% (corresponding to 0.8 part of DHPO in 90 parts of the residual liquor).

The MIBK solution was obtained from the mixer-settler No. 1 in a proportion of 211 parts on the average per hour and its DHPO and CHPO-contents were 4.83% (corresponding to 10.2 parts of DHPO in 211 parts of the MIBK solution) and 0.38%, respectively. After all, of 11.3 parts of DHPO contained in 100 parts of the aqueous caustic soda solution, 10.2 parts of DHPO was extracted into the MIBK layer and 0.8 part remained in the residual alkali liquor. Therefore the retention rate of DHPO on extraction was 97%.

The MIBK solution thus obtained gave a high purity resorcinol in a high yield by cleavage reaction of the solution.

Completely the same result was obtained even when methyl isopropyl ketone or isopropyl ether was used in place of MIBK.

EXAMPLE 2

The extracting operation was carried out in the same manner as described in Example 1 except that the aqueous caustic soda solution as a material was replaced by the liquor which was obtained after recycling the residual alkali liquor obtained in Example 1 five to 10 times to the extraction step of oxidation solution.

The DHPO- and CHPO-contents of the thus obtained caustic soda liquor were 10.8 and 0.4%, respectively.

As the result, the MIBK solution containing 4.55% of DHPO and 0.43% of CHPO was obtained in a proportion of 211 parts on the avarage per hour (corresponding to 9.6 parts of DHPO). On the other hand, the yield of the residual aqueous alkali liquor containing 0.67% of DHPO was 89.5 parts (corresponding to 0.6 part of DHPO). The retention rate of DHPO was 94%.

REFERENCE EXAMPLE 1

Extraction operation was carried out on a two-stage mixer-settler type extractor, using completely the same aqueous caustic soda solution (DHPO content 11.3%, CHPO content 0.5%) as used in Example 1 and MIBK as an extracting solvent.

The extracting temperature at each plate was set up at 80° C. Feed amounts of the two materials, MIBK and aqueous caustic soda solution, were 120 parts/hr and 100 parts/hr, respectively.

After the extracting operation, the amount of the MIBK solution (DHPO content 6.72%, CHPO content 1.30%, DCA content 0.31%) obtained was 131 parts on the average per hour (corresponding to 8.79 parts of DHPO). That of the residual aqueous alkali liquor (DHPO content 0.71%) was 90 parts on the average per hour (corresponding to 0.71 part of DHPO). The retention rate of DHPO was 84%.

REFERENCE EXAMPLE 2

The extracting operation was carried out in the same manner as described in Reference example 1 except that the aqueous caustic soda solution as a material was replaced by the liquor which was obtained after recycling the residual alkali liquor obtained in Reference example 1 five to ten times to the extraction step of oxidation solution.

The DHPO- and CHPO-contents of the thus obtained caustic soda liquor were 10.6, and 0.5%, respectively.

After the extracting operation, the amount of the methyl isobutyl ketone solution (DHPO-content 4.07%, CHPO content 3.07%, DCA content 0.61%) obtained was 130 parts per hour (corresponding to 5.3 parts of DHPO). That of the residual aqueous caustic soda liquor (DHPO content 0.56%) was 89 parts per hour (corresponding to 0.5 part of DHPO). The retention rate of DHPO was 55%.

What is claimd is:

1. A method for extracting a dihydroperoxide of a dialkylbenzene of the formula,

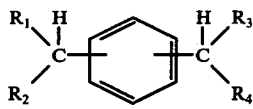

wherein each $R_1$, $R_2$, $R_3$ and $R_4$ is independently isopropyl or sec.butyl, from an aqueous alkali solution of the said dihydroperoxide with at least one organic solvent selected from the group consisting of $C_4$–$C_{10}$ ketones, $C_4$–$C_{10}$ ethers and $C_4$–$C_8$ alcohols, which comprises extracting the dihydroperoxide by a countercurrent multi-stage extraction with a temperature gradient between each stage and with all of the extractions being conducted at a temperature of from 0° to 85° C, the aqueous alkali solution being fed to the lower temperature zone, the organic solvent being fed to the higher temperature zone with said lower temperature being from 0° to 50° C, and said higher temperature being from 50° to 85° C, and each aqueous alkali solution and organic solvent being fed countercurrently, whereby the dihydroperoxide is obtained in the form of organic solvent solution from the lower temperature zone.

2. The method according to claim 1, wherein the multi-stage has two to 12 theoretical plates.

3. The method according to claim 1, wherein the amount of the organic solvent is one to five times the weight of the aqueous alkali solution.

4. The method according to claim 1, wherein the concentration of the dihydroperoxide in the aqueous alkali solution is 3 to 20% by weight.

5. The method according to claim 1, wherein the aqueous alkali solution of the dihydroperoxide is freed from oxidation by-products having 2-hydroxy-2-propyl group.

6. A method for extracting a dihydroperoxide of a dialkylbenzene of the formula,

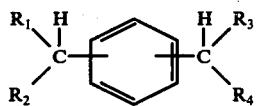

wherein each $R_1$, $R_2$, $R_3$ and $R_4$ is independently isopropyl or sec.-butyl, from an aqueous alkali solution of the said dihydroperoxide, which comprises feeding the aqueous alkali solution to one side of an extraction zone together with countercurrent feed of at least one organic solvent selected from the group consisting of $C_4$–$C_{10}$ ketones, $C_4$–$C_{10}$ ethers and $C_4$–$C_8$ alcohols to the other side of extraction zone, the extraction zone having a multi-stage with a temperature gradient between each stage and with all of the extractions being conducted at a temperature from 0° to 85° C, the aqueous alkali solution being fed to a lower temperature zone, and the organic solvent being fed to a higher temperature zone with said lower temperature being from 0° to 50° C, and said higher temperature being from 50° to 85° C, whereby the dihydroperoxide is obtained in the form of the organic solvent solution from the lower temperature zone.

* * * * *